United States Patent
Uehara et al.

(10) Patent No.: US 12,134,741 B2
(45) Date of Patent: Nov. 5, 2024

(54) METHODS FOR INTEGRATED SEPARATION OF DIENES

(71) Applicant: SABIC Global Technologies B.V., Bergen op Zoom (NL)

(72) Inventors: Ernesto Uehara, Riyadh (SA); Mohammed Al-Ghamdi, Jubail (SA); Vivek Singh Solanki, Jubail (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 142 days.

(21) Appl. No.: 17/777,489

(22) PCT Filed: Sep. 23, 2020

(86) PCT No.: PCT/IB2020/058878
§ 371 (c)(1),
(2) Date: May 17, 2022

(87) PCT Pub. No.: WO2021/099856
PCT Pub. Date: May 27, 2021

(65) Prior Publication Data
US 2023/0357653 A1 Nov. 9, 2023

Related U.S. Application Data

(60) Provisional application No. 62/937,096, filed on Nov. 18, 2019.

(51) Int. Cl.
C07C 7/04 (2006.01)
C07C 2/42 (2006.01)
(Continued)

(52) U.S. Cl.
CPC .............. *C10G 69/126* (2013.01); *C07C 2/42* (2013.01); *C07C 4/22* (2013.01); *C07C 5/03* (2013.01);
(Continued)

(58) Field of Classification Search
CPC .............. C10G 69/12; C07C 2/42; C07C 4/22
See application file for complete search history.

(56) References Cited

U.S. PATENT DOCUMENTS 3,719,718 A * 3/1973 Grude ....................... C07C 4/22
585/354
2003/0100809 A1* 5/2003 Tian .......................... C07C 2/44
585/350

(Continued)

OTHER PUBLICATIONS

International Search Report for International Application No. PCT/IB2020/058878; International Filing Date Sep. 23, 2020; Date of Mailing Nov. 25, 2020; 4 pages.
(Continued)

*Primary Examiner* — Sharon Pregler
(74) *Attorney, Agent, or Firm* — CANTOR COLBURN LLP

(57) ABSTRACT

Systems and methods for processing a $C_4$ and $C_5$ stream are disclosed. A pygas stream can be separated in a depentanizer to produce a $C_4$ and $C_5$ stream and a $C_6$ to $C_9+$ stream. The $C_4$ and $C_5$ stream is further processed to recover $C_5$ dienes including isoprene, pentadiene, cyclopentadiene, or combinations thereof. The $C_6$ to $C_9+$ stream is further processed to recover aromatics including benzene, toluene, xylene, ethylbenzene, or combinations thereof.

17 Claims, 6 Drawing Sheets

(51) Int. Cl.
*C07C 4/22* (2006.01)
*C07C 5/03* (2006.01)
*C10G 7/06* (2006.01)
*C10G 69/12* (2006.01)

(52) U.S. Cl.
CPC .................. *C07C 7/04* (2013.01); *C10G 7/06* (2013.01); *C10G 2300/1003* (2013.01); *C10G 2400/22* (2013.01); *C10G 2400/30* (2013.01)

(56) References Cited

U.S. PATENT DOCUMENTS

2019/0031967 A1* 1/2019 Alabbad ................ C10G 65/16
2019/0225560 A1 7/2019 Abdelghani

OTHER PUBLICATIONS

Written Opinion for International Application No. PCT/IB2020/058878; International Filing Date Sep. 23, 2020; Date of Mailing Nov. 25, 2020; 6 pages.

* cited by examiner

METHODS FOR INTEGRATED SEPARATION OF DIENES

CROSS REFERENCE TO RELATED APPLICATIONS

This application is a National Stage application of PCT/IB2020/058878, filed Sep. 23, 2020, which claims the benefit of priority of U.S. Provisional Patent Application No. 62/937,096, filed Nov. 18, 2019, both of which are hereby incorporated by reference in their entireties herein.

FIELD OF INVENTION

The present invention generally relates to systems and methods for processing a $C_4$ to $C_{12}$ hydrocarbon stream. More specifically, the present invention relates to systems and methods for producing $C_5$ dienes and other high value chemicals from pyrolysis gasoline (pygas) obtained by steam cracking hydrocarbons.

BACKGROUND OF THE INVENTION

Pygas is a by-product of high-temperature steam cracking (750-950° C.) of hydrocarbons to produce products such as ethylene and propylene. Pygas is a naphtha-range product containing $C_5$ to $C_{12}$ aromatics, di-olefins, olefins, and paraffins. Conventionally, pygas is hydrogenated in a gas hydrotreating unit (GHIU) to saturate the di-olefins, which are unstable, and then the pygas is further processed to produce finished $C_6$-$C_8$ products such as benzene, toluene, and xylene (BTX), as well as hydrogenated $C_5$ hydrocarbons. The hydrogenated $C_5$ hydrocarbons are then recycled to the steam cracking unit. The process also involves separating a hydrogenated $C_9+$ stream as wash oil and fuel oil.

$C_5$ dienes in pygas, such as isoprene, cyclopentadiene, and pentadiene, are highly valued. The conventional method of processing pygas converts high value $C_5$ dienes in the pygas to form low value $C_5$ paraffins. Therefore, it fails to maximize the value of processing pygas. Furthermore, the conventional method for processing pygas often suffers from fouling of the separation equipment due to polymerization of the dienes in the pygas stream, reducing the efficiency of pygas processing.

Overall, while the systems and methods for processing pygas exist, the need for improvements in this field persists in light of at least the aforementioned drawbacks of the conventional systems and methods.

BRIEF SUMMARY OF THE INVENTION

A solution to at least some of the above-mentioned problems associated with systems and methods for processing pygas has been discovered. The solution resides in a method of processing pygas that includes separating the pygas to form a $C_4$ stream and a $C_5$ stream, and separating $C_5$ dienes from the $C_5$ stream. This is beneficial for at least increasing the overall value of the pygas as $C_5$ dienes are high value chemicals. Furthermore, the remaining $C_5$ hydrocarbons, after separation of the $C_5$ dienes, are in a mixture with $C_4$ hydrocarbons, and this mixture can be hydrogenated and recycled back to a steam cracking unit. This further increases the utilization rate of the hydrocarbons in pygas. Additionally, according to embodiments of the invention, the disclosed method includes injecting 4-tert-butylcatechol (TBC) into distillation columns used in the separation process so as to mitigate fouling of the distillation equipment, thereby increasing the production efficiency of high value chemicals from pygas. Therefore, the method and system of the present invention provides a technical solution to at least some of the problems associated with the conventional systems and methods for processing pygas mentioned above.

Embodiments of the invention include a method of processing a hydrocarbon stream. The method comprises (a) separating a $C_4$-$C_5$ stream to produce a $C_4$ stream comprising $C_4$ hydrocarbons and a $C_5$ stream comprising $C_5$ hydrocarbons. The method comprises (b) processing the $C_5$ stream in a dimerization unit under reaction conditions sufficient to dimerize cyclopentadiene of the $C_5$ stream and form a reactor product stream comprising dicyclopentadiene and $C_5$ hydrocarbons. The method comprises (c) separating the reactor product stream to produce a top product stream comprising $C_5$ hydrocarbons and a bottom product stream comprising dicyclopentadiene.

Embodiments of the invention include a method of processing pygas. The method comprises separating the pygas to produce a $C_4$-$C_5$ stream comprising $C_4$ and $C_5$ hydrocarbons and a $C_6$-$C_9+$ stream comprising $C_6+$ hydrocarbons. The method comprises separating the $C_4$-$C_5$ stream to produce a $C_4$ stream comprising $C_4$ hydrocarbons and a $C_5$ stream comprising $C_5$ hydrocarbons. The method comprises processing the $C_5$ stream in a dimerization unit under reaction conditions sufficient to dimerize cyclopentadiene of the $C_5$ stream and form a reactor product stream comprising $C_5$ hydrocarbons and dicyclopentadiene. The method comprises separating the reactor product stream to produce a top product stream comprising $C_5$ hydrocarbons and a bottom product stream comprising dicyclopentadiene. The method comprises separating the top product stream to produce a first product stream comprising isoprene, a second product stream comprising pentadiene, and a $C_5$ raffinate comprising pentanes, pentenes, and/or piperlynes. The method comprises processing the $C_5$ raffinate in a first hydrogenation unit to hydrogenate the pentenes and/or piperlynes. The method comprises processing the $C_4$ stream in the first hydrogenation unit under reaction conditions sufficient to saturate unsaturated $C_4$ hydrocarbons of the $C_4$ stream. The method comprises separating the $C_6$-$C_9+$ stream in a deheptanizer to produce a $C_6$-$C_7$ stream comprising $C_6$ and $C_7$ hydrocarbons and a $C_8$-$C_9+$ stream comprising $C_8$ and $C_9+$ hydrocarbons. The method comprises processing the $C_6$-$C_7$ stream in a second hydrogenation unit under reaction conditions sufficient to produce benzene and toluene. The method comprises separating the $C_8$-$C_9+$ stream in a deoctanizer to produce a $C_8$ stream comprising $C_8$ hydrocarbons and a $C_9+$ stream comprising unhydrogenated $C_9+$ hydrocarbons. The method comprises processing the $C_5$ stream in a styrene separation unit to produce a xylene stream comprising primarily xylene and a styrene stream comprising primarily styrene.

Embodiments of the invention include a method of processing pygas. The method includes separating the pygas to produce a $C_4$-$C_5$ stream comprising $C_4$ and $C_5$ hydrocarbons and a $C_6$-$C_9+$ stream comprising $C_6+$ hydrocarbons. The method comprises separating the $C_4$-$C_5$ stream to produce a $C_4$ stream comprising $C_4$ hydrocarbons and a $C_5$ stream comprising $C_5$ hydrocarbons. The method comprises processing the $C_5$ stream in a dimerization unit under reaction conditions sufficient to dimerize cyclopentadiene of the $C_5$ stream and form a reactor product stream comprising $C_5$ hydrocarbons and dicyclopentadiene. The method comprises separating the reactor product stream to produce a top product stream comprising $C_5$ hydrocarbons and a bottom product stream comprising dicyclopentadiene. The method comprises separating the top product stream to produce a first product stream comprising isoprene, a second product stream comprising pentadiene, and a $C_5$ raffinate comprising pentanes, pentenes, and/or piperlynes. The method comprises processing the $C_5$ raffinate in a first hydrogenation unit to hydrogenate the pentenes and/or piperlynes. The method comprises processing the $C_4$ stream in the first hydrogenation unit under reaction conditions sufficient to saturate unsaturated $C_4$ hydrocarbons of the $C_4$ stream. The method comprises processing the $C_6$-$C_9$+ stream in a second hydrogenation unit under reaction conditions sufficient to produce a hydrogenated $C_6$-$C_9$+ stream. The method comprises separating the hydrogenated $C_6$-$C_9$+ stream to produce a fuel gas stream comprising primarily fuel gas and purified $C_6$-$C_9$+ stream. The method comprises separating the purified $C_6$-$C_9$+ stream in a deoctanizer to produce a hydrogenated $C_6$-$C_8$ stream comprising benzene, toluene, xylene, and ethylbenzene, a hydrogenated wash oil stream, and a hydrogenated fuel oil stream.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The term "$C_n$+ hydrocarbon" wherein n is a positive integer, e.g. 1, 2, 3, 4, or 5, as that term is used in the specification and/or claims, means any hydrocarbon having at least n number of carbon atom(s) per molecule.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

In the context of the present invention at least twenty embodiments are now described. Embodiment 1 is a method of processing a hydrocarbon stream The method includes the steps of (a) separating a $C_4$-$C_5$ stream to produce a $C_4$ stream including $C_4$ hydrocarbons and a $C_5$ stream including $C_5$ hydrocarbons; (b) processing the $C_5$ stream in a dimerization unit under reaction conditions sufficient to dimerize cyclopentadiene of the $C_5$ stream and form a reactor product stream including dicyclopentadiene and $C_5$ hydrocarbons; and (c) separating the reactor product stream to produce a top product stream including $C_5$ hydrocarbons and a bottom product stream including dicyclopentadiene. Embodiment 2 is the method of embodiment 1, further including the steps of (d) separating the top product stream to produce a first product stream containing isoprene, a second product stream containing pentadiene, and a $C_5$ raffinate containing pentanes, pentenes, and/or piperlynes; and (e) processing the $C_5$ raffinate in a hydrogenation unit to hydrogenate the pentenes and/or piperlynes. Embodiment 3 is the method of embodiment 2, further including the step of (f) processing the $C_4$ stream in a hydrogenation unit under reaction conditions sufficient to saturate unsaturated $C_4$ hydrocarbons of the $C_4$ stream. Embodiment 4 is the method of embodiment 3, wherein step (e) and step (f) are conducted in the same hydrogenation unit. Embodiment 5 is the method of any of embodiments 1 to 4, further including the step of: (g) monomerizing the dicyclopentadiene of the bottom product stream in a reactive distillation column to produce a cyclopentadiene stream containing at least 99 wt. % cyclopentadiene. Embodiment 6 the method of embodiment 5, further including the step of: (h) dimerizing the cyclopentadiene of the cyclopentadiene stream to produce a dicyclopentadiene stream containing at least 97 wt. % dicyclopentadiene. Embodiment 7 is the method of embodiment 6, wherein the dimerizing of the cyclopentadiene of step (h) is conducted in a reactor having a shell-and-tube configuration. Embodiment 8 the method of any of embodiments 1 to 7, wherein the reaction conditions in step (b) comprise a reaction temperature in a range of 95 to 110° C. Embodiment 9 the method of any of embodiments 1 to 8, wherein step (c) is conducted in a vacuum distillation column. Embodiment 10 is the method of any of embodiments 1 to 9, wherein the $C_4$-$C_5$ stream is obtained from pygas. Embodiment 11 is the method of embodiment 10, wherein the $C_4$-$C_5$ stream is obtained by separating the pygas, which further produces a $C_6$-$C_9$+ stream containing $C_6$+ hydrocarbons. Embodiment 12 is the method of embodiment 11, further including the step of (i) processing the $C_6$-$C_9$+ stream to produce BTX and/or ethylbenzene. Embodiment 13 is the method of embodiment 12, wherein the processing in step (i) comprises: (j) separating the $C_6$-$C_9$+ stream in a deheptanizer to produce a $C_6$-$C_7$ stream containing $C_6$ and $C_7$ hydrocarbons and a $C_8$-$C_9$+ stream containing $C_5$ hydrocarbons and $C_9$+ hydrocarbons; (k) processing the $C_6$-$C_7$ stream in a hydrogenation unit under reaction conditions sufficient to produce benzene and toluene. Embodiment 14 is the method of embodiment 13, further including the steps of (1) separating the $C_8$-$C_9$+ stream in a deoctanizer to produce a $C_5$ stream containing $C_5$ hydrocarbons and a $C_9$+ stream containing unhydrogenated $C_9$+ hydrocarbons; and (m) processing the $C_5$ stream in a styrene separation unit to produce a xylene stream containing xylene and a styrene stream containing primarily styrene. Embodiment 15 is the method of embodiment 12, wherein the processing in step (i) includes (n)

separating the $C_6$-$C_9$+ stream in a deoctanizer to produce a $C_6$-$C_8$ stream containing $C_6$ to $C_8$ hydrocarbons and a $C_9$+ stream containing unhydrogenated $C_9$+ hydrocarbons; and (o) processing the $C_6$-$C_8$ stream in a hydrogenation unit under reaction conditions sufficient to produce benzene, toluene, xylene, and ethylbenzene. Embodiment 16 is the method of embodiment 12, wherein the processing in step (i) comprises: (p) processing the $C_6$-$C_9$+ stream in a hydrogenation unit under reaction conditions sufficient to produce a hydrogenated $C_6$-$C_9$+ stream; and (q) separating the hydrogenated $C_6$-$C_9$+ stream in a deoctanizer to produce a hydrogenated $C_6$-$C_8$ stream containing benzene, toluene, xylene, and ethylbenzene. Embodiment 17 is the method of embodiment 16, wherein the separating in step (q) further produces hydrogenated wash oil and hydrogenated fuel oil.

Embodiment 18 is a method of processing pygas. This method includes the steps of separating the pygas to produce a $C_4$-$C_5$ stream containing $C_4$ and $C_5$ hydrocarbons and a $C_6$-$C_9$+ stream containing $C_6$+ hydrocarbons; separating the $C_4$-$C_5$ stream to produce a $C_4$ stream containing $C_4$ hydrocarbons and a $C_5$ stream containing $C_5$ hydrocarbons; processing the $C_5$ stream in a dimerization unit under reaction conditions sufficient to dimerize cyclopentadiene of the $C_5$ stream and form a reactor product stream containing $C_5$ hydrocarbons and dicyclopentadiene; separating the reactor product stream to produce a top product stream containing $C_5$ hydrocarbons and a bottom product stream containing dicyclopentadiene; separating the top product stream to produce a first product stream containing isoprene, a second product stream containing pentadiene, and a $C_5$ raffinate containing pentanes, pentenes, and/or piperlynes; processing the $C_5$ raffinate in a first hydrogenation unit to hydrogenate the pentenes and/or piperlynes; processing the $C_4$ stream in the first hydrogenation unit under reaction conditions sufficient to saturate unsaturated $C_4$ hydrocarbons of the $C_4$ stream; separating the $C_6$-$C_9$+ stream in a deheptanizer to produce a $C_6$-$C_7$ stream containing $C_6$ and $C_7$ hydrocarbons and a $C_8$-$C_9$+ stream containing $C_8$ and $C_9$+ hydrocarbons; processing the $C_6$-$C_7$ stream in a second hydrogenation unit under reaction conditions sufficient to produce benzene and toluene; separating the $C_8$-$C_9$+ stream in a deoctanizer to produce a $C_8$ stream containing $C_8$ hydrocarbons and a $C_9$+ stream containing unhydrogenated $C_9$+ hydrocarbons; and processing the $C_8$ stream in a styrene separation unit to produce a xylene stream containing primarily xylene and a styrene stream containing primarily styrene. Embodiment 19 is the method of embodiment 18, further including the steps of monomerizing the dicyclopentadiene of the bottom product stream in a reactive distillation column to produce a cyclopentadiene stream containing at least 99 wt. % cyclopentadiene; and dimerizing the cyclopentadiene of the cyclopentadiene stream to produce a dicyclopentadiene stream containing at least 97 wt. % dicyclopentadiene.

Embodiment 20 is a method of processing pygas. The method includes the steps of separating the pygas to produce a $C_4$-$C_5$ stream containing $C_4$ and $C_5$ hydrocarbons and a $C_6$-$C_9$+ stream containing $C_6$+ hydrocarbons; separating the $C_4$-$C_5$ stream to produce a $C_4$ stream containing $C_4$ hydrocarbons and a $C_5$ stream containing $C_5$ hydrocarbons; processing the $C_5$ stream in a dimerization unit under reaction conditions sufficient to dimerize cyclopentadiene of the $C_5$ stream and form a reactor product stream containing $C_5$ hydrocarbons and dicyclopentadiene; separating the reactor product stream to produce a top product stream containing $C_5$ hydrocarbons and a bottom product stream containing dicyclopentadiene; separating the top product stream to produce a first product stream containing isoprene, a second product stream containing pentadiene, and a $C_5$ raffinate containing pentanes, pentenes, and/or piperlynes; processing the $C_5$ raffinate in a first hydrogenation unit to hydrogenate the pentenes and/or piperlynes; processing the $C_4$ stream in the first hydrogenation unit under reaction conditions sufficient to saturate unsaturated $C_4$ hydrocarbons of the $C_4$ stream; processing the $C_6$-$C_9$+ stream in a second hydrogenation unit under reaction conditions sufficient to produce a hydrogenated $C_6$-$C_9$+ stream; separating the hydrogenated $C_6$-$C_9$+ stream to produce a purified $C_6$-$C_9$+ stream and a fuel gas stream; and separating the purified $C_6$-$C_9$+ stream in a deoctanizer to produce a hydrogenated $C_6$-$C_8$ stream containing benzene, toluene, xylene, and ethylbenzene, a hydrogenated wash oil stream, and a hydrogenated fuel oil stream.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which:

FIG. 2A shows a flow chart of a method of processing pygas using a system shown in FIG. 1A; FIG. 2B shows a flow chart of a method of processing pygas using a system shown in FIG. 1B; FIG. 2C shows a flow chart of a method of processing pygas using a system shown in FIG. 1C.

DETAILED DESCRIPTION OF THE INVENTION

Currently, pygas, which contains $C_5$ to $C_{12}$ hydrocarbons, is processed in a hydrotreating unit to saturate unstable hydrocarbons to produce paraffins and BTX. During the process, high value chemicals including $C_5$ dienes are converted to low value $C_5$ paraffins, therefore, there is a loss of valuable products in pygas processing. Furthermore, the separation equipment used in the conventional pygas processing method often suffers fouling due to polymerization of the dienes. The present invention provides a solution to at least some of these problems. The solution is premised on a method of processing pygas that includes separating the pygas into a $C_4$ and $C_5$ stream and a $C_6$+ stream using a deheptanizer, thereby mitigating the fouling of separation equipment. The disclosed method further includes separating $C_5$ dienes in individual product streams before the hydrogenation step, thereby increasing the value of the products recovered overall from the processing of pygas. Moreover, the disclosed method includes dimerizing cyclopentadiene in a $C_5$ stream and separating the dicyclopentadiene from other $C_5$ hydrocarbons to recover cyclopentadiene, thereby reducing the energy needed for directly separating cyclopentadiene from other $C_5$ hydrocarbons having close boiling points to cyclopentadiene. These and other non-limiting aspects of the present invention are discussed in further detail in the following sections.

A. System for Processing Pygas

Figure 1A:
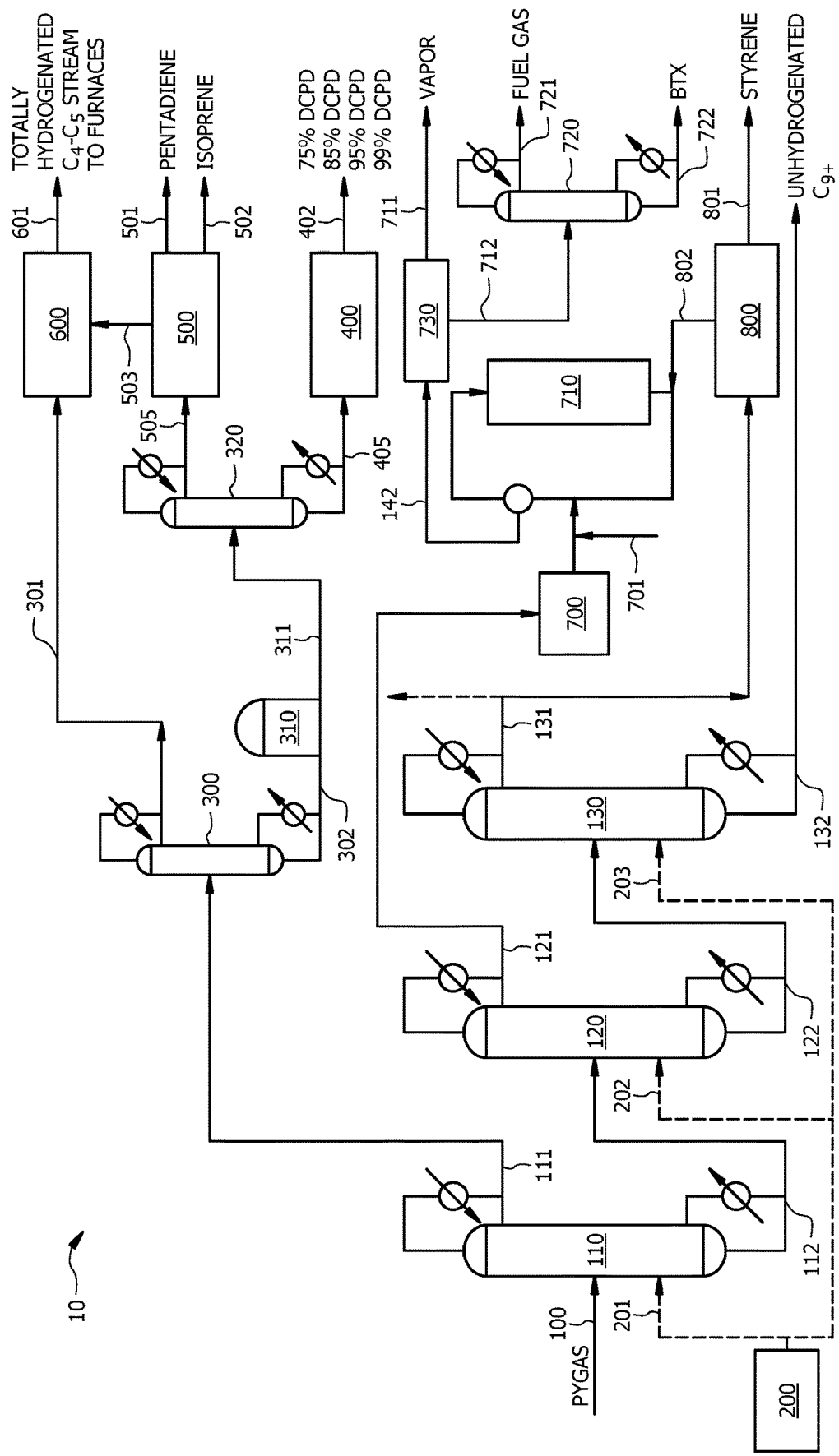
FIG. 1A shows a schematic diagram of a system for processing pygas and recovering $C_5$ dienes, BTX, and styrene, according to embodiments of the invention.
Figure 1B:
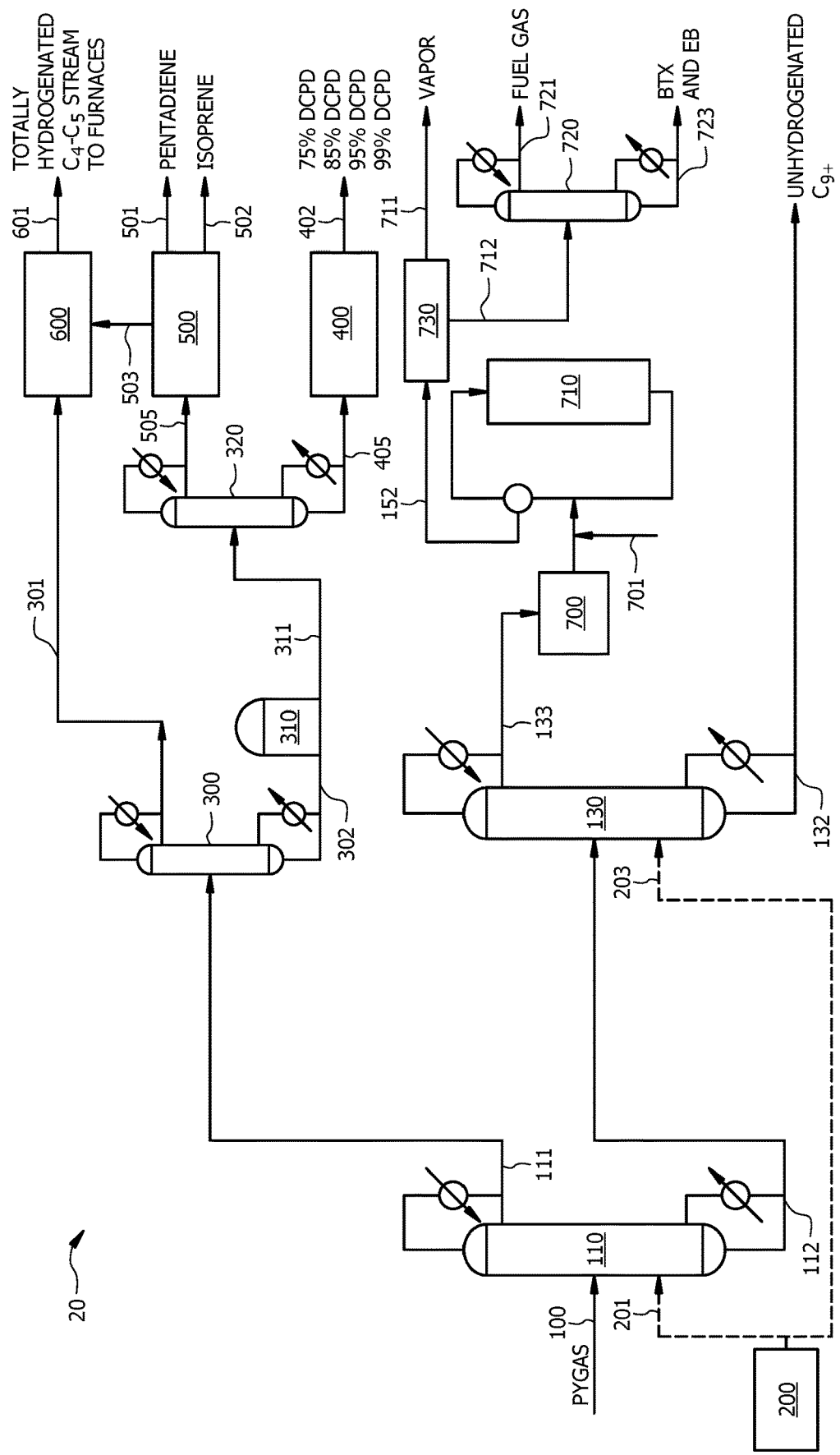
FIG. 1B shows a schematic diagram of a system for processing pygas and recovering $C_5$ dienes, ethylbenzene, and BTX, according to embodiments of the invention.
Figure 1C:
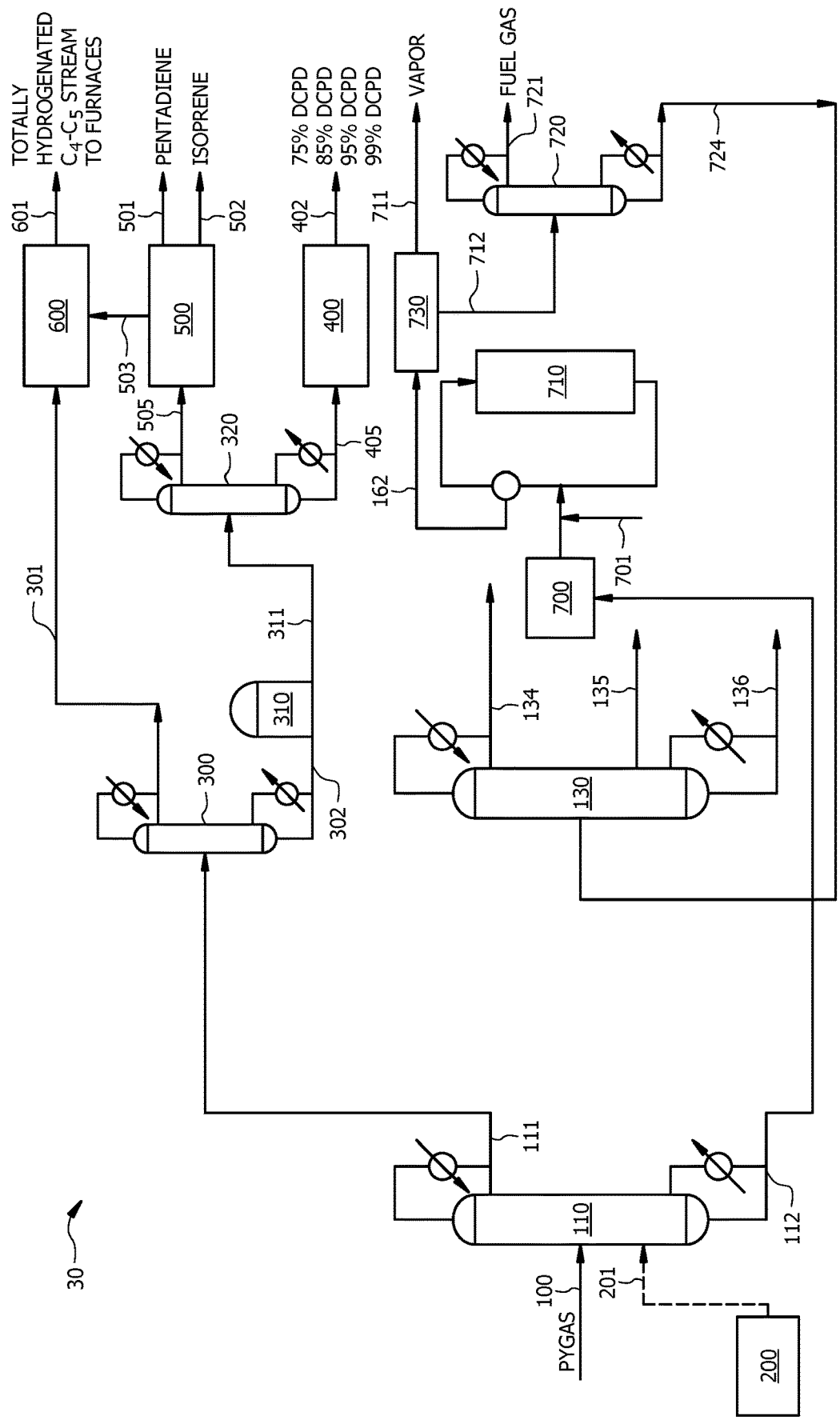
FIG. 1C shows a schematic diagram of a system for processing pygas and recovering $C_5$ dienes, BTX, and hydrogenated wash oil, according to embodiments of the invention.

In embodiments of the invention, a system for processing pygas includes a depentanizer, units for recovering $C_4$ and $C_5$ hydrocarbons, and units for recovering $C_6$+. With reference to FIGS. 1A-1C, schematic diagrams are shown for system 10, 20, and 30, respectively, which can be used for processing pygas to recover high value chemicals including $C_5$ dienes, and aromatics.

According to embodiments of the invention, system 10 comprises depentanizer 110 configured to separate a hydrocarbon stream to form $C_4$-$C_5$ stream 111 comprising $C_4$ and $C_5$ hydrocarbons, and $C_6$-$C_9$+ stream 112 comprising $C_6$+ hydrocarbons. In embodiments of the invention, the hydrocarbon stream includes pygas stream 100. In embodiments of the invention, depentanizer 110 includes one or more distillation columns. A top outlet of depentanizer 110 may be in fluid communication with an inlet of debutanizer 300 such that $C_4$-$C_5$ stream 111 flows from depentanizer 110 to debutanizer 300. In embodiments of the invention, debutanizer 300 is configured to separate $C_4$-$C_5$ stream 111 to produce $C_4$ stream 301 comprising $C_4$ hydrocarbons and $C_5$ stream 302 comprising $C_5$ hydrocarbons.

A bottom outlet of debutanizer 300 may be in fluid communication with dimerization reactor 310 such that $C_5$ stream 302 flows from debutanizer 300 to dimerization reactor 310. In embodiments of the invention, dimerization reactor 310 is configured to react cyclopentadiene of $C_5$ stream 302 to produce dicyclopentadiene in reactor product stream 311. An outlet of dimerization reactor 310 may be in fluid communication with vacuum depentanizer 320 such that reactor product stream 311 flows from dimerization reactor 310 to vacuum depentanizer 320. In embodiments of the invention, vacuum depentanizer 320 includes one or more vacuum distillation columns configured to separate reactor product stream 311 to produce top product stream 505 comprising $C_5$ hydrocarbons and bottom product stream 405 comprising primarily dicyclopentadiene. A bottom outlet of vacuum depentanizer 320 may be in fluid communication with DCPD purification unit 400 such that dicyclopentadiene flows from vacuum depentanizer 320 to DCPD purification unit 400, which is configured to purify dicyclopentadiene of bottom product stream 405 to form dicyclopentadiene stream 402. Dicyclopentadiene stream 402 may include more than 75 wt. % dicyclopentadiene. A top outlet of vacuum depentanizer 320 is in fluid communication with $C_5$ diene separation unit 500 such that top product stream 505 flows from vacuum depentanizer 320 to $C_5$ diene separation unit 500. $C_5$ diene separation unit 500 may be configured to separate top product stream 505 to form second product stream 501 comprising primarily pentadiene, and first product stream 502 comprising primarily isoprene.

In embodiments of the invention, $C_5$ diene separation unit 500 includes one or more distillation columns and/or one or more extractive distillation columns. One or more distillation columns of $C_5$ diene separation unit 500 may be configured to recover piperlyne and isoprene. One or more extractive distillation columns may be configured to recover isoprene.

A top outlet of debutanizer 300 may be in fluid communication with first hydrogenation unit 600 such that $C_4$ stream 301 flows from debutanizer 300 to first hydrogenation unit 600. In embodiments of the invention, an outlet of $C_5$ diene separation unit 500 is in fluid communication with an inlet of first hydrogenation unit 600 such that $C_5$ rafffinate stream 503 comprising non-diene $C_5$ hydrocarbons flows from $C_5$ diene separation unit 500 to first hydrogenation unit 600. According to embodiments of the invention, first hydrogenation unit 600 is configured to hydrogenate at least some unsaturated hydrocarbons of $C_4$ stream 301 and/or $C_5$ raffinate stream 503 to form hydrogenated $C_4$ and $C_5$ stream 601 comprising hydrogenated $C_4$ and/or $C_5$ hydrocarbons. In embodiments of the invention, an outlet of first hydrogenation unit 600 is in fluid communication with a steam cracking unit such that the hydrogenated $C_4$ and/or $C_5$ hydrocarbons of $C_4$ and $C_5$ stream 601 are steam cracked. The steam cracking unit may be the steam cracking unit that produces pygas stream 100.

According to embodiments of the invention, a bottom outlet of depentanizer 110 is in fluid communication with deheptanizer 120 such that $C_6$-$C_9$+ stream 112 flows from depentanizer 110 to deheptanizer 120. Deheptanizer 120 may be configured to separate $C_6$-$C_9$+ stream 112 to produce $C_6$-$C_7$ stream 121 comprising $C_6$ and $C_7$ hydrocarbons and $C_8$-$C_9$+ stream 122 comprising $C_8$ and $C_9$+ hydrocarbons. In embodiments of the invention, atop outlet of deheptanizer 120 is in fluid communication with feed drum 700 for second hydrogenation unit 710 such that $C_6$-$C_7$ stream 121 flows from deheptanizer 120 to second hydrogenation unit 710. Hydrogen stream 701 comprising primarily hydrogen may be combined with $C_6$-$C_7$ stream 121 and flowed into second hydrogenation unit 710. Second hydrogenation unit 710 may be configured to hydrogenate hydrocarbons of $C_6$-$C_7$ stream 121 to form at least a portion of hydrogenated $C_6$-$C_7$ stream 142 comprising benzene and toluene. In embodiments of the invention, an outlet of second hydrogenation unit 710 is in fluid communication with an inlet of separator 730 such that hydrogenated $C_6$-$C_7$ stream 142 flows to separator 730. Separator 730 may be configured to separate hydrogenated $C_6$-$C_7$ stream 142 to produce vapor stream 711 and liquid stream 712. Liquid stream 712 may flow to stabilizer 720, configured to separate liquid stream 712 to form fuel gas stream 721 comprising primarily fuel gas and BTX stream 722 comprising primarily BTX. In embodiments of the invention, stabilizer 720 comprises one or more distillation columns.

According to embodiments of the invention, a bottom outlet of deheptanizer 120 is in fluid communication with an inlet of deoctanizer 130 such that $C_8$-$C_9$+ stream 122 flows from deheptanizer 120 to deoctanizer 130. Deoctanizer 130 may be configured to separate $C_8$-$C_9$+ stream 122 to produce $C_8$ stream 131 comprising $C_8$ hydrocarbons and $C_9$+ stream 132 comprising unhydrogenated $C_9$+ hydrocarbons. In embodiments of the invention, an top outlet of deoctanizer 130 is in fluid communication with styrene separation unit 800 such that $C_8$ stream 131 flows from deoctanizer 130 to styrene separation unit 800. Styrene separation unit 800 may be configured to separate $C_8$ stream 131 to produce styrene stream 801 comprising primarily styrene and xylene stream 802 comprising primarily xylene. In embodiments of the invention, xylene stream 802 may be combined with an effluent of second hydrogenation unit 710 to form hydrogenated $C_6$ to $C_7$ stream 142. According to embodiments of the invention, system 10 includes one or more TBC packages comprising 4-tert-butylcatechol (TBC). TBC packages 200 may be in fluid communication with depentanizer 110, deheptanizer 120, and/or deoctanizer 130 such that 4-tert-butylcatechol (TBC) is injected in depentanizer 110, deheptanizer 120, and/or deoctanizer 130 via stream 201, stream 202, and/or stream 203, respectively System 20 comprises all the units and equipment as arranged in system 10 except system 20 can be designed not to include deheptanizer 120 and/or styrene separation unit 800. In embodiments of the invention, in system 20, a bottom outlet of depentanizer 110 is in fluid communication with an inlet of deoctanizer 130 such that $C_6$ to $C_9+$ stream 112 flows from depentanizer 110 to deoctanizer 130. Deoctanizer 130 of system 20 may be configured to separate $C_6$ to $C_9+$ stream 112 to form $C_6$ to $C_8$ stream 133 comprising $C_6$ to $C_8$ hydrocarbons and $C_9+$ stream 132 comprising primarily unhydrogenated $C_9+$ hydrocarbons. A top outlet of deoctanizer 130 may be in fluid communication with feed drum 700 such that $C_6$ to $C_8$ stream 133 is fed to second hydrogenation unit 710. Second hydrogenation unit 710 may be configured to hydrogenate hydrocarbons of $C_6$-$C_8$ stream 133 to form hydrogenated $C_6$-$C_8$ stream 152 comprising benzene, toluene, xylene, ethylbenzene, or combinations thereof. In embodiments of the invention, an outlet of second hydrogenation unit 710 is in fluid communication with separator 730 configured to separate hydrogenated $C_6$-$C_8$ stream 152 to form vapor stream 711 and liquid stream 712. Liquid stream 712 may be separated in stabilizer 720 to form fuel gas stream 721 comprising fuel gas and aromatic stream 723 comprising benzene, toluene, xylene, and ethylbenzene.

System 30 comprises all the units and equipment as system 20. In embodiments of the invention, in system 30, a bottom outlet of depentanizer 110 may be in fluid communication with feed drum 700 such that $C_6$ to $C_9+$ stream 112 flows from depentanizer 110 to second hydrogenation unit 710. Second hydrogenation unit 710 may be configured to hydrogenate $C_6$ to $C_9+$ stream 112 to form hydrogenated $C_6$ to $C_9+$ stream 162. An outlet of second hydrogenation unit 710 may be in fluid communication with separator 730 such that hydrogenated $C_6$ to $C_9+$ stream 162 flows from second hydrogenation unit 710 to separator 730. Separator 730 may be configured to separate hydrogenated $C_6$ to $C_9+$ stream 162 to form vapor stream 711 and liquid stream 712. Liquid stream 712 may be separated in stabilizer 720 to form fuel gas stream 721 comprising fuel gas and purified $C_6$ to $C_9+$ stream 724 comprising hydrogenated $C_6$ to $C_9+$ hydrocarbons. In embodiments of the invention, an outlet of stabilizer 720 is in fluid communication with an inlet of deoctanizer 130 such that purified $C_6$ to $C_9+$ stream 724 flows from stabilizer 720 to deoctanizer 130. Deoctanizer 130 of system 30 may be configured to separate purified $C_6$ to $C_9+$ stream 724 to produce hydrogenated $C_6$ to $C_8$ stream 134 comprising primarily hydrogenated $C_6$ to $C_8$ hydrocarbons, hydrogenated wash oil stream 135 comprising hydrogenated wash oil, and fuel oil stream 136 comprising hydrogenated $C_9+$ fuel oil.

B. Method of Processing Pygas

Figure 2A:
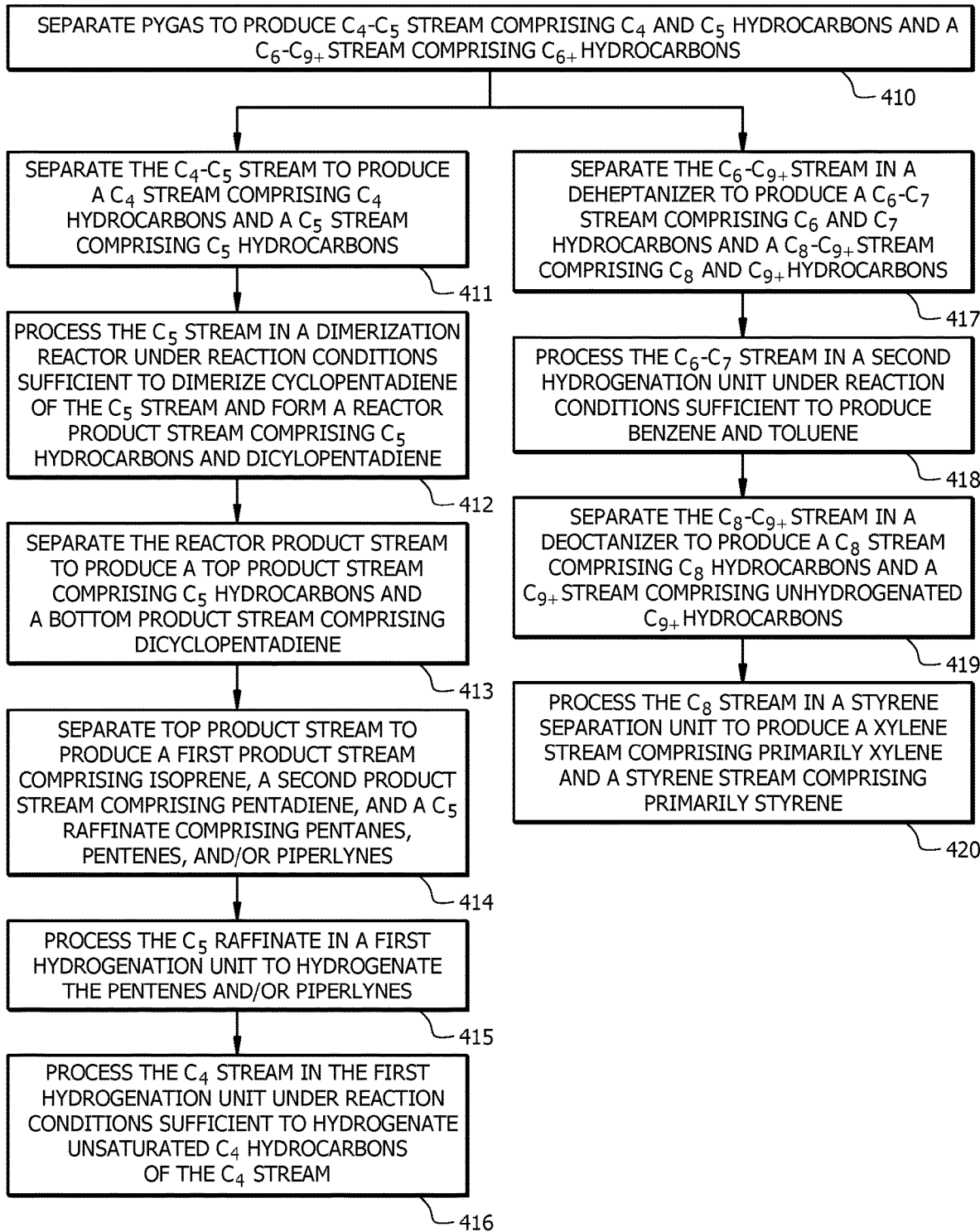
FIGS. 2A to 2C show flowcharts for methods of processing pygas, according to embodiments of the invention.

Methods for processing hydrocarbons, including pygas, have been discovered. As shown in FIG. 2A, embodiments of the invention include method 40 for processing pygas. Method 40 may be implemented by system 10, as shown in FIG. 1A and described above.

According to embodiments of the invention, as shown in block 410, method 40 includes separating pygas stream 100 in depentanizer 110 to produce $C_4$-$C_5$ stream 111 comprising $C_4$ and $C_5$ hydrocarbons and a $C_6$-$C_9+$ stream 112 comprising $C_6+$ hydrocarbons. Depentanizer 110 may be operated at an overhead boiling temperature range of 20 to 60° C. and a reboiler temperature range of 80 to 120° C. The operating pressure of depentanizer 110 may be in a range of 0.75 to 1.25 bar and all ranges and values there between including ranges of 0.75 to 0.80 bar, 0.80 to 0.85 bar, 0.85 to 0.90 bar, 0.90 to 0.95 bar, 0.95 to 1.00 bar, 1.00 to 1.05 bar, 1.05 to 1.10 bar, 1.10 to 1.15 bar, 1.15 to 1.20 bar, and 1.20 to 1.25 bar. In embodiments of the invention, $C_4$ hydrocarbons in $C_4$-$C_5$ stream 111 include n-butane, isobutane, butadiene, 1-butene, 2-butenes, isobutene, or combinations thereof. $C_5$ hydrocarbons in $C_4$-$C_5$ stream 111 may include pentanes, iso-pentanes, cyclopentanes, pentenes, iso-pentenes, cyclopentenes, iso-pentadiene, pentyene, pentadiene (piperlene), cyclopentadiene, isoprene, or combinations thereof According to embodiments of the invention, as shown in block 411, method 40 includes separating, in debutanizer 300, $C_4$-$C_5$ stream 111 to produce $C_4$ stream 301 comprising $C_4$ hydrocarbons and $C_5$ stream 302 comprising $C_5$ hydrocarbons. Debutanizer 300 may be operated at an overhead boiling temperature range of 20 to 60° C. and a reboiler temperature range of 80 to 120° C. The operating pressure of debutanizer 300 may be in a range of 4 to 10 bar and all ranges and values there between including ranges of 4 to 5 bar, 5 to 6 bar, 6 to 7 bar, 7 to 8 bar, 8 to 9 bar, and 9 to 10 bar.

According to embodiments of the invention, as shown in block 412, method 40 comprises processing $C_5$ stream 503 in dimerization reactor 310 under reaction conditions sufficient to dimerize cyclopentadiene of $C_5$ stream 503 and form reactor product stream 311 comprising $C_5$ hydrocarbons and dicyclopentadiene. In embodiments of the invention, at least 15 wt. % cyclopentadiene of $C_5$ stream 302 is dimerized at block 412. In embodiments of the invention, at block 412, dimerization reactor 310 is operated at a temperature in a range of 95 to 110° C. and all ranges and values there between including ranges of 95 to 98° C., 98 to 101° C., 101 to 104° C., 104 to 107° C., and 107 to 110° C.

According to embodiments of the invention, as shown in block 413, method 40 comprises separating, in vacuum depentanizer 320, reactor product stream 311 to produce top product stream 505 comprising $C_5$ hydrocarbons and bottom product stream 405 comprising dicyclopentadiene. In embodiments of the invention, vacuum depentanizer 320 is operated at an overhead boiling temperature range of 20 to 60° C. and a reboiler temperature range of 120 to 160° C. The operating pressure of vacuum depentanizer 320 may be in a range of 0.2 to 0.6 bar and all ranges and values there between including ranges of 0.2 to 0.3 bar, 0.3 to 0.4 bar, 0.4 to 0.5 bar, and 0.5 to 0.6 bar. In embodiments of the invention, the dicyclopentadiene of bottom product stream 405 is further purified in DCPD purification unit 400 to form dicylopentaidene stream 402 comprising at least 75 wt. % dicyclopentadiene. The dicyclopentadiene in dicyclopentadiene stream 402 may be further monomerized in a reactive distillation column to produce a cyclopentadiene stream comprising at least 99.0 wt. % cyclopentadiene. The cyclopentadiene produced by monomerization in the reactive distillation column may be further dimerized to produce a dicyclopentadiene stream comprising at least 97 wt. % dicyclopentadiene. In embodiments of the invention, the cyclopentadiene produced by monomerization in the reactive distillation column may be further dimerized in a reactor having a shell-and-tube configuration.

According to embodiments of the invention, as shown in block 414, method 40 includes separating, in $C_5$ diene separation unit 500, top product stream 505 to produce first product stream 502 comprising isoprene, second product stream 501 comprising pentadiene, and $C_5$ raffinate 503 comprising pentanes, pentenes, and/or piperlynes. In embodiments of the invention, $C_5$ diene separation unit 500 includes one or more distillation columns for recovering pentadiene. The one or more distillation columns for recovering pentadiene may be operated at an overhead boiling temperature range of 10 to 30° C. and a reboiler temperature range of 35 to 75° C. The operating pressure of the one or more distillation columns for recovering pentadiene may be in a range of 0.5 to 1.5 bar and all ranges and values there between. In embodiments of the invention, $C_5$ diene separation unit 500 includes one or more extractive distillation columns in series for recovering isoprene. The one or more extractive distillation columns may be operated at an overhead boiling temperature range of 30 to 70° C. and a reboiler temperature range of 110 to 150° C. The operating pressure of the one or more extractive distillation columns for recovering isoprene may be in a range of 1.2 to 2.0 bar and all ranges and values there between including ranges of 1.2 to 1.4 bar, 1.4 to 1.6 bar, 1.6 to 1.8 bar, and 1.8 to 2.0 bar. The one or more extractive distillation columns may be operated using a solvent including acetronitrile, dimethylformamide, N-methyl-2-pyrrolidone, or combinations thereof.

According to embodiments of the invention, as shown in block 415, method 40 includes processing, in first hydrogenation unit 600, $C_5$ raffinate 503 under reaction conditions sufficient to hydrogenate the pentenes and/or piperlynes of $C_5$ raffinate 503. According to embodiments of the invention, as shown in block 416, method 40 includes processing $C_4$ stream 301 in first hydrogenation unit 600 under reaction conditions sufficient to hydrogenate unsaturated $C_4$ hydrocarbons of $C_4$ stream 301. In embodiments of the invention, first hydrogenation unit 600 at blocks 415 and 416 is operated at an reaction temperature of 40 to 140° C. and an operating pressure of 20 to 40 bar. Processing at blocks 415 and 416 is performed in the presence of a catalyst comprising $Ni/Al_2O_3$, $Pd/Al_2O_3$, or combinations thereof. According to embodiments of the invention, the processing at block 415 and 416 is carried out concurrently in the same unit.

According to embodiments of the invention, as shown in block 417, method 40 comprises separating $C_6$-$C_9$+ stream in deheptanizer 120 to produce $C_6$-$C_7$ stream 121 comprising $C_6$ and $C_7$ hydrocarbons and $C_8$-$C_9$+ stream 122 comprising $C_8$ and $C_9$+ hydrocarbons. In embodiments of the invention, deheptanizer 120 at block 417 is operated at an overhead boiling temperature range of 20 to 60° C. and a reboiler temperature range of 75 to 110° C. Deheptanizer 120 may be operated at an operating pressure of 0.5 to 1.0 bar and all ranges and values there between including ranges of 0.5 to 0.6 bar, 0.6 to 0.7 bar, 0.7 to 0.8 bar, 0.8 to 0.9 bar, and 0.9 to 1.0 bar.

According to embodiments of the invention, as shown in block 418, method 40 comprises processing $C_6$-$C_7$ stream 121 in second hydrogenation unit 710 under reaction conditions sufficient to produce benzene and toluene in hydrogenated $C_6$-$C_7$ stream 142. In embodiments of the invention, at block 418, second hydrogenation unit 710 is operated at a reaction temperature of 100 to 200° C. and an operating pressure of 10 to 30 bar. Processing at block 418 may be performed in the presence of a catalyst comprising $Ni/Al_2O_3$, $Pd/Al_2O_3$, or combinations thereof.

According to embodiments of the invention, as shown in block 419, method 40 comprises separating $C_8$-$C_9$+ stream 122 in deoctanizer 130 to produce $C_8$ stream 131 comprising $C_8$ hydrocarbons and $C_9$+ stream 132 comprising unhydrogenated $C_9$+ hydrocarbons. In embodiments of the invention, deoctanizer 130 is operated at an overhead boiling temperature range of 20 to 60° C. and a reboiler temperature range of 70 to 100° C. Deoctanizer 130 may be operated at an operating pressure of 0.04 to 1.0 bar and all ranges and values there between including ranges of 0.04 to 0.2 bar, 0.2 to 0.4 bar, 0.4 to 0.6 bar, 0.6 to 0.8 bar, and 0.8 to 1.0 bar. In embodiments of the invention, at blocks 417 to 419, TBC is injected in depentanizer 110, deheptanizer 120, and/or deoctanizer 130 to mitigate fouling of equipment.

According to embodiments of the invention, as shown in block 420, method 40 includes processing $C_8$ stream 131 in a styrene separation unit to produce xylene stream 802 comprising primarily xylene and styrene stream 801 comprising primarily styrene. In embodiments, processing at block 420 may include liquid-liquid extraction, azeotropic distillation, extractive distillation, membrane separation, or combinations thereof. In embodiments of the invention, xylene stream 802 is combined with an effluent of second hydrogenation unit 710 to form hydrogenated $C_6$-$C_7$ stream 142. The combined stream may be further separated in separator 730 to produce vapor stream 711 and liquid stream 712. Liquid stream 712 may be separated in stabilizer 720 to produce fuel gas stream 721 comprising fuel gas, and BTX stream 722 comprising BTX. As an alternative to, in addition to, processing at block 420, $C_8$ stream 131 may be combined with $C_6$-$C_7$ stream 121 and the combined stream containing styrene may be hydrogenated in second hydrogenation unit 710 to convert styrene into ethylbenzene (EB).

Figure 2B:
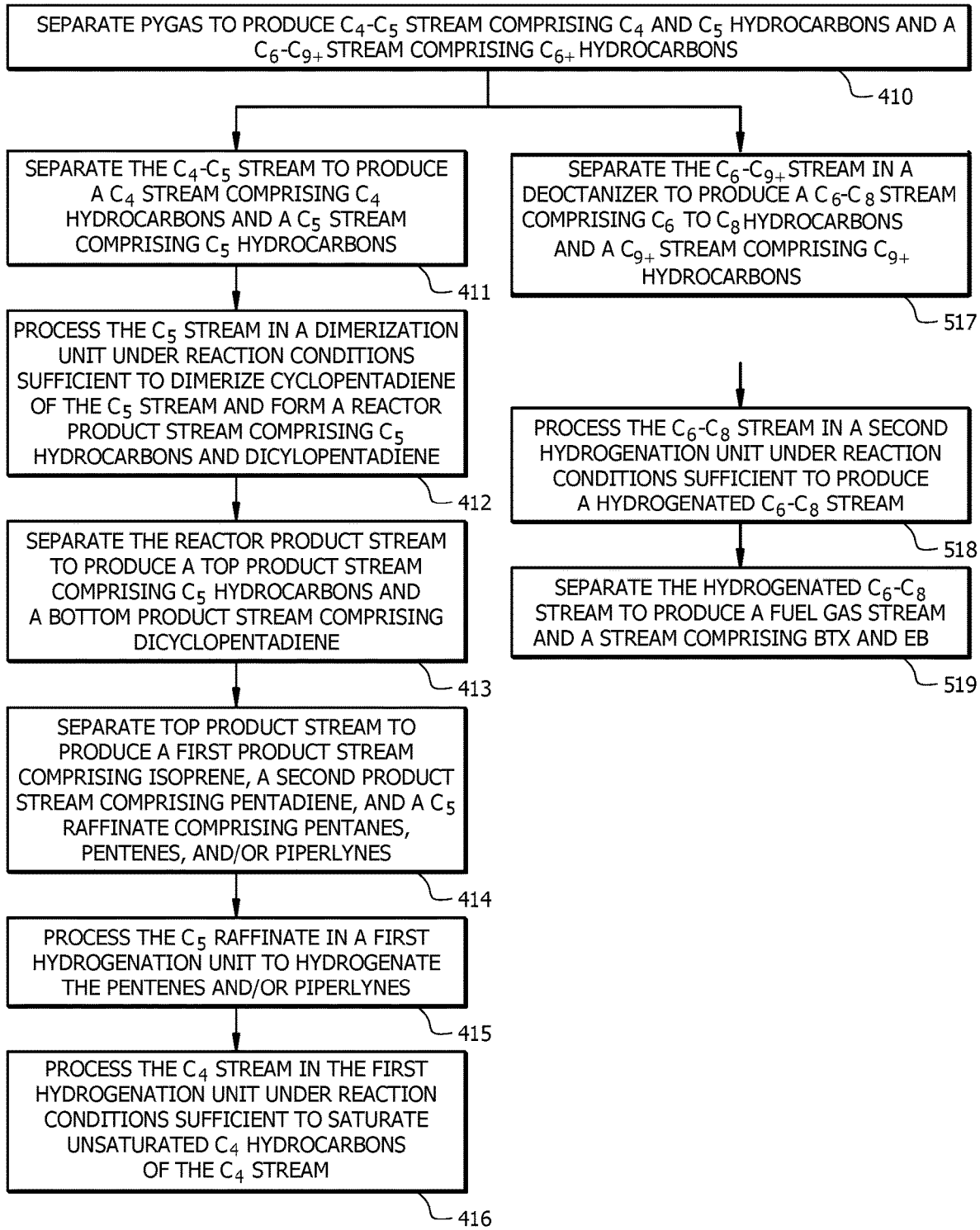

As shown in FIG. 2B, embodiments of the invention include method 50 for processing pygas. Method 50 may be implemented by system 20, as shown in FIG. 2B and described above. According to embodiments of the invention, method 50 includes blocks 411 to 416 of method 40 as described above. In embodiments of the invention, as shown in block 517, method 50 includes separating $C_6$-$C_9$+ stream 112 in deoctanizer 130 to produce $C_6$-$C_8$ stream 133 comprising $C_6$ to $C_8$ hydrocarbons and $C_9$+ stream 132 comprising unhydrogenated $C_9$+ hydrocarbons. In embodiments of the invention, at block 517, deoctanizer 130 is operated at an overhead boiling temperature range of 20 to 60° C. and a reboiler temperature range of 70 to 100° C. At block 517, deoctanizer 130 may be operated at an operating pressure of 0.04 to 1.0 bar and all ranges and values there between including ranges of 0.04 to 0.2 bar, 0.2 to 0.4 bar, 0.4 to 0.6 bar, 0.6 to 0.8, and 0.8 to 1.0 bar.

In embodiments of the invention, as shown in block 518, method 50 further includes processing $C_6$-$C_8$ stream 133 in second hydrogenation unit 710 under reaction conditions sufficient to produce hydrogenated $C_6$-$C_8$ stream 152. At block 518, second hydrogenation unit 710 may be operated at a reaction temperature of 100 to 200° C. and an operating pressure of 10 to 30 bar.

In embodiments of the invention, as shown in block 519, method 50 further includes separating hydrogenated $C_6$-$C_8$ stream 152 to produce fuel gas stream 721 comprising fuel gas and aromatic stream 723 comprising BTX and ethylbenzene (EB). In embodiments of the invention, separating at block 519 includes separating, in separator 730, hydrogenated $C_6$-$C_8$ stream 152 to produce vapor stream 711 comprising $H_2O$, $H_2$, and liquid stream 712, and separating liquid stream 712 in stabilizer 720 to produce fuel gas stream 721 and aromatic stream 723. At block 519, separator 730 is operated at an overhead boiling temperature range of 80 to 100° C., a reboiler temperature range of 100 to 120° C., and an operating pressure of 1 to 2 bar. At block 519, stabilizer 720 is operated at an overhead boiling temperature range of 20 to 60° C., a reboiler temperature range of 120 to 200° C., and an operating pressure of 6 to 10 bar.

Figure 2C:
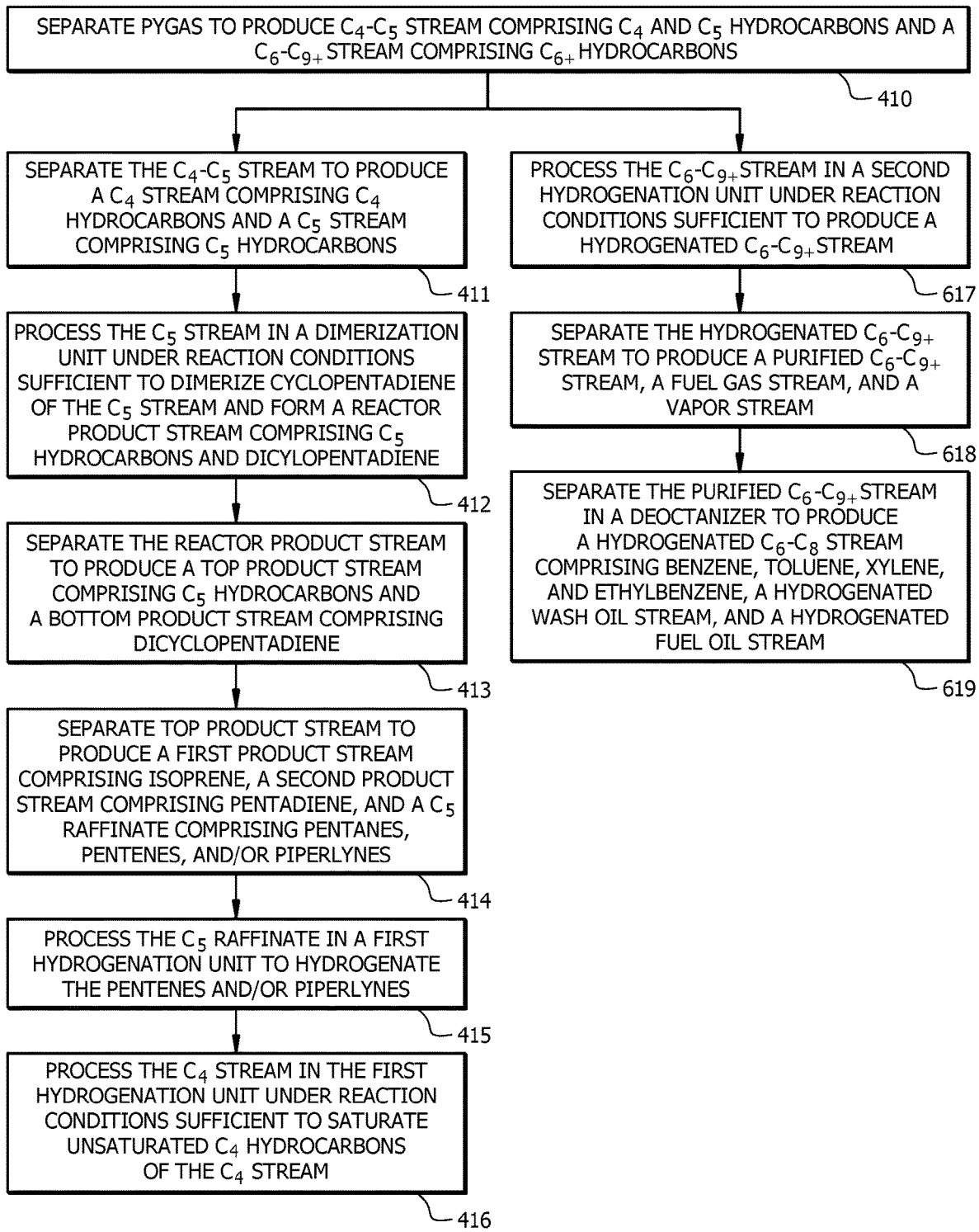

As shown in FIG. 2C, embodiments of the invention include method 60 for processing pygas. Method 60 may be implemented by system 30, as shown in FIG. 2C and described above. According to embodiments of the invention, method 60 includes blocks 411 to 416 of method 40 as described above. In embodiments of the invention, as shown in block 617, method 60 further includes processing $C_6$-$C_9$+ stream 112 in second hydrogenation unit 710 under reaction conditions sufficient to produce hydrogenated $C_6$-$C_9$+ stream 162. At block 617, second hydrogenation unit 710 may be operated at a reaction temperature of 100 to 200° C. and an operating pressure of 10 to 20 bar. In embodiments of the invention, as shown in block 618, method 60 includes separating hydrogenated $C_6$-$C_9$+ stream 162 to produce purified $C_6$-$C_9$+ stream 724. In embodiments of the invention, separating at block 618 includes separating hydrogenated $C_6$-$C_9$+ stream 162 in separator 730 to produce vapor stream 711 and liquid stream 712, and separating liquid stream 712 in stabilizer 720 to produce purified $C_6$-$C_9$+ stream 724 comprising at least 90 wt. % $C_6$-$C_9$+ hydrocarbons and fuel gas stream 721 comprising fuel gas. At block 618, separator 730 is operated at an overhead boiling temperature range of 80 to 100° C., a reboiler temperature range of 100 to 120° C., and an operating pressure of 1 to 2 bar. At block 618, stabilizer 720 is operated at an overhead boiling temperature range of 20 to 60° C., a reboiler temperature range of 120 to 200° C., and an operating pressure of 6 to 10 bar.

In embodiments of the invention, as shown in block 619, method 60 includes separating purified $C_6$-$C_9$+ stream 724 in deoctanizer 130 to produce (a) hydrogenated $C_6$-$C_8$ stream 134 comprising benzene, toluene, xylene, ethylbenzene, or combinations thereof, (b) hydrogenated wash oil stream 135 comprising hydrogenated wash oil, and (c) hydrogenated fuel oil stream 136 comprising hydrogenated $C_9$+ fuel oil. According to embodiments of the invention, at block 619, deoctanizer 130 is operated at an overhead boiling temperature range of 20 to 60° C., a reboiler temperature range of 70 to 100° C. At block 619, deoctanizer 130 is operated with an operating pressure of 0.04 to 1.0 bar.

Although embodiments of the present invention have been described with reference to blocks of FIGS. 2A to 2C should be appreciated that operation of the present invention is not limited to the particular blocks and/or the particular order of the blocks illustrated in FIGS. 2A to 2C. Accordingly, embodiments of the invention may provide functionality as described herein using various blocks in a sequence different than that of FIGS. 2A to 2C.

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

As part of the disclosure of the present invention, specific examples are included below. The examples are for illustrative purposes only and are not intended to limit the invention. Those of ordinary skill in the art will readily recognize parameters that can be changed or modified to yield essentially the same results.

Example 1

Simulation of a Method of Processing Pygas

Simulations for the processing of pygas were conducted in ASPEN platform. The pygas composition used in the simulations is shown in Tables 1 and 2.

TABLE 1

Pygas compositions based on carbon numbers

| CUT COMPONENTS | wt % MIN | wt % MAX |
| --- | --- | --- |
| C4 COMPONENTS | 0.00 | 1.35 |
| C5 COMPONENTS | 11.60 | 24.46 |
| C6 COMPONENTS | 29.96 | 50.63 |
| C7 COMPONENTS | 7.09 | 11.97 |
| C8 COMPONENTS | 9.07 | 15.33 |
| C9+ COMPONENTS | 15.52 | 26.23 |

TABLE 2

Weight fraction of dienes in pygas

| DIENES | wt % MIN | wt % MAX |
| --- | --- | --- |
| ISOPRENE | 1.89 | 3.20 |
| CYCLOPENTADIENE | 3.50 | 5.92 |
| PENTADIENE | 1.40 | 2.37 |
| BENZENE | 25.40 | 42.93 |
| TOLUENE | 7.01 | 11.84 |
| EBENZENE | 1.96 | 3.31 |
| XYLENES | 1.36 | 2.30 |
| STYRENE | 4.43 | 7.49 |
| C9+ DIENES | 6.90 | 11.67 |

The simulations were run based on the schematic diagram of system 10 as shown in FIG. 1A. The results show that with a pygas flow rate between 322.4 ktA to 572.0 ktA, about 6.2 to 10.4 ktA pentadiene was produced, about 8.3 to 14.1 ktA isoprene was produced, and about 15.4 to 26.1 ktA dicyclopentadiene was produced. Furthermore, the simulation results further show that the system produced about 19.5 to 32.9 ktA styrene, 153.9 to 260.0 ktA BTX, and 20.7 to 34.9 ktA fuel gas. Furthermore, the simulation results show that about 74.1 to 125.3 ktA unhydrogenated $C_9$+ hydrocarbon was produced, and 30.4 to 51.3 ktA $C_9$+ dienes were produced.

Example 2

Simulations for the processing of pygas were conducted in ASPEN platform. The pygas composition used in the simulations is shown in Tables 1 and 2.

The simulations were run based on the schematic diagram of system 20 as shown in FIG. 1B. The results show that with a pygas flow rate between 322.4 ktA to 572.0 ktA, about 6.2 to 10.4 ktA pentadiene was produced, about 8.3 to 14.1 ktA isoprene was produced, and about 15.4 to 26.1 ktA dicyclopentadiene was produced. Furthermore, the simulation results further show that the system produced about 173.4 to 292.9 ktA BTX, and 20.7 to 34.9 ktA fuel gas. Furthermore, the simulation results show that about 74.1 to 125.3 ktA unhydrogenated $C_9$+ hydrocarbon was produced, and 30.4 to 51.3 ktA $C_9$+ dienes were produced.

Example 3

Simulations for the processing of pygas were conducted in ASPEN platform. The pygas composition used in the simulations is shown in Tables 1 and 2.

The simulations were run based on the schematic diagram of system 30 as shown in FIG. 1C. The results show that with a pygas flow rate between 322.4 ktA to 572.0 ktA, about 6.2 to 10.4 ktA pentadiene was produced, about 8.3 to 14.1 ktA isoprene was produced, and about 15.4 to 26.1 ktA dicyclopentadiene was produced. Furthermore, the simulation results show that the system produced about 173.4 to 292.9 ktA hydrogenated $C_6$ to $C_8$+, and 20.7 to 34.9 ktA fuel gas. Furthermore, the simulation results show that about 74.1 to 125.3 ktA unhydrogenated $C_9$+ hydrocarbon was produced, and 29.6 to 50.1 ktA $C_9$+ fuel oil was produced. Additionally, the simulation results show that about 44.5 to 75.2 ktA hydrogenated wash oil was produced.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of processing a hydrocarbon stream, the method comprising:
   (a1) separating a pygas into a $C_4$-$C_5$ stream and a $C_6$-$C_9$+ stream comprising $C_6$+ hydrocarbons
   (a2) separating the $C_4$-$C_5$ stream to produce a $C_4$ stream comprising $C_4$ hydrocarbons and a $C_5$ stream comprising $C_5$ hydrocarbons;
   (b) processing the $C_5$ stream in a dimerization unit under reaction conditions sufficient to dimerize cyclopentadiene of the $C_5$ stream and form a reactor product stream comprising dicyclopentadiene and $C_5$ hydrocarbons; and
   (c) separating the reactor product stream to produce a top product stream comprising $C_5$ hydrocarbons and a bottom product stream comprising dicyclopentadiene, and
   (g) monomerizing the dicyclopentadiene of the bottom product stream in a reactive distillation column to produce a cyclopentadiene stream comprising at least 99 wt. % cyclopentadiene.

2. The method of claim 1, further comprising:
   (d) separating the top product stream to produce a first product stream comprising isoprene, a second product stream comprising pentadiene, and a $C_5$ raffinate comprising pentanes, pentenes, and/or piperlynes; and
   (e) processing the $C_5$ raffinate in a hydrogenation unit to hydrogenate the pentenes and/or piperlynes.

3. The method of claim 2, further comprising:
   (f) processing the $C_4$ stream in a hydrogenation unit under reaction conditions sufficient to saturate unsaturated $C_4$ hydrocarbons of the $C_4$ stream.

4. The method of claim 3, wherein step (e) and step (f) are conducted in the same hydrogenation unit.

5. The method of claim 1, further comprising:
   (h) dimerizing the cyclopentadiene of the cyclopentadiene stream to produce a dicyclopentadiene stream comprising at least 97 wt. % dicyclopentadiene.

6. The method of claim 5, wherein the dimerizing of the cyclopentadiene of step (h) is conducted in a reactor having a shell-and-tube configuration.

7. The method of claim 1, wherein the reaction conditions in step (b) comprise a reaction temperature in a range of 95 to 110° C.

8. The method of claim 1, wherein step (c) is conducted in a vacuum distillation column.

9. The method of claim 1, further comprising:
   (i) processing the $C_6$-$C_9$+ stream to produce BTX and/or ethylbenzene.

10. The method of claim 9, wherein the processing in step (i) comprises:
    (j) separating the $C_6$-$C_9$+ stream in a deheptanizer to produce a $C_6$-$C_7$ stream comprising $C_6$ and $C_7$ hydrocarbons and a $C_8$-$C_9$+ stream comprising $C_8$ hydrocarbons and $C_9$+ hydrocarbons;
    (k) processing the $C_6$-$C_7$ stream in a hydrogenation unit under reaction conditions sufficient to produce benzene and toluene.

11. The method of claim 10, further comprising:
    (l) separating the $C_8$-$C_9$+ stream in a deoctanizer to produce a $C_8$ stream comprising $C_8$ hydrocarbons and a $C_9$+ stream comprising unhydrogenated $C_9$+ hydrocarbons; and
    (m) processing the $C_8$ stream in a styrene separation unit to produce a xylene stream comprising xylene and a styrene stream comprising primarily styrene.

12. The method of claim 9, wherein the processing in step (i) comprises:
    (n) separating the $C_6$-$C_9$+ stream in a deoctanizer to produce a $C_6$-$C_8$ stream comprising $C_6$ to $C_8$ hydrocarbons and a $C_9$+ stream comprising unhydrogenated $C_9$+ hydrocarbons; and
    (o) processing the $C_6$-$C_8$ stream in a hydrogenation unit under reaction conditions sufficient to produce benzene, toluene, xylene, and ethylbenzene.

13. The method of claim 9, wherein the processing in step (i) comprises:
    (p) processing the $C_6$-$C_9$+ stream in a hydrogenation unit under reaction conditions sufficient to produce a hydrogenated $C_6$-$C_9$+ stream;
    (q) separating the hydrogenated $C_6$-$C_9$+ stream in a deoctanizer to produce a hydrogenated $C_6$-$C_8$ stream comprising benzene, toluene, xylene, and ethylbenzene.

14. The method of claim 13, wherein the separating in step (q) further produces hydrogenated wash oil and hydrogenated fuel oil.

15. A method of processing pygas, the method comprising:
    separating the pygas to produce a $C_4$-$C_5$ stream comprising $C_4$ and $C_5$ hydrocarbons and a $C_6$-$C_9$+ stream comprising $C_6$+ hydrocarbons;
    separating the $C_4$-$C_5$ stream to produce a $C_4$ stream comprising $C_4$ hydrocarbons and a $C_5$ stream comprising $C_5$ hydrocarbons;

processing the $C_5$ stream in a dimerization unit under reaction conditions sufficient to dimerize cyclopentadiene of the $C_5$ stream and form a reactor product stream comprising $C_5$ hydrocarbons and dicyclopentadiene;

separating the reactor product stream to produce a top product stream comprising $C_5$ hydrocarbons and a bottom product stream comprising dicyclopentadiene;

separating the top product stream to produce a first product stream comprising isoprene, a second product stream comprising pentadiene, and a $C_5$ raffinate comprising pentanes, pentenes, and/or piperlynes;

processing the $C_5$ raffinate in a first hydrogenation unit to hydrogenate the pentenes and/or piperlynes;

processing the $C_4$ stream in the first hydrogenation unit under reaction conditions sufficient to saturate unsaturated $C_4$ hydrocarbons of the $C_4$ stream;

separating the $C_6$-$C_9$+ stream in a deheptanizer to produce a $C_6$-$C_7$ stream comprising $C_6$ and $C_7$ hydrocarbons and a $C_8$-$C_9$+ stream comprising $C_8$ and $C_9$+ hydrocarbons;

processing the $C_6$-$C_7$ stream in a second hydrogenation unit under reaction conditions sufficient to produce benzene and toluene;

separating the $C_8$-$C_9$+ stream in a deoctanizer to produce a $C_8$ stream comprising $C_8$ hydrocarbons and a $C_9$+ stream comprising unhydrogenated $C_9$+ hydrocarbons; and processing the $C_8$ stream in a styrene separation unit to produce a xylene stream comprising primarily xylene and a styrene stream comprising primarily styrene.

16. The method of claim 15, further comprising:

monomerizing the dicyclopentadiene of the bottom product stream in a reactive distillation column to produce a cyclopentadiene stream comprising at least 99 wt. % cyclopentadiene; and dimerizing the cyclopentadiene of the cyclopentadiene stream to produce a dicyclopentadiene stream comprising at least 97 wt. % dicyclopentadiene.

17. A method of processing pygas, the method comprising:

separating the pygas to produce a $C_4$-$C_5$ stream comprising $C_4$ and $C_5$ hydrocarbons and a $C_6$-$C_9$+ stream comprising $C_6$+ hydrocarbons;

separating the $C_4$-$C_5$ stream to produce a $C_4$ stream comprising $C_4$ hydrocarbons and a $C_5$ stream comprising $C_5$ hydrocarbons;

processing the $C_5$ stream in a dimerization unit under reaction conditions sufficient to dimerize cyclopentadiene of the $C_5$ stream and form a reactor product stream comprising $C_5$ hydrocarbons and dicyclopentadiene;

separating the reactor product stream to produce a top product stream comprising $C_5$ hydrocarbons and a bottom product stream comprising dicyclopentadiene;

separating the top product stream to produce a first product stream comprising isoprene, a second product stream comprising pentadiene, and a $C_5$ raffinate comprising pentanes, pentenes, and/or piperlynes;

processing the $C_5$ raffinate in a first hydrogenation unit to hydrogenate the pentenes and/or piperlynes;

processing the $C_4$ stream in the first hydrogenation unit under reaction conditions sufficient to saturate unsaturated $C_4$ hydrocarbons of the $C_4$ stream;

processing the $C_6$-$C_9$+ stream in a second hydrogenation unit under reaction conditions sufficient to produce a hydrogenated $C_6$-$C_9$+ stream;

separating the hydrogenated $C_6$-$C_9$+ stream to produce a purified $C_6$-$C_9$+ stream and a fuel gas stream; and separating the purified $C_6$-$C_9$+ stream in a deoctanizer to produce a hydrogenated $C_6$-$C_8$ stream comprising benzene, toluene, xylene, and ethylbenzene, a hydrogenated wash oil stream, and a hydrogenated fuel oil stream.

* * * * *